US00PP11810P2

(12) United States Plant Patent
Saville

(10) Patent No.: US PP11,810 P2
(45) Date of Patent: Mar. 13, 2001

(54) MINIATURE ROSE PLANT NAMED 'SAVANADE'

(75) Inventor: F. Harmon Saville, deceased, late of Newburyport, MA (US), by Charles K. Brown, executor

(73) Assignee: Nor'East Miniature Roses, Inc., Rowley, MA (US)

( * ) Notice: Under 35 U.S.C. 154(b), the term of this patent shall be extended for 0 days.

(21) Appl. No.: 08/991,982

(22) Filed: Dec. 17, 1997

(51) Int. Cl.[7] ..... A01H 5/00

(52) U.S. Cl. ..... Plt./125

(58) Field of Search ..... Plt./125, 118, 145

*Primary Examiner*—Howard J. Locker

(57) ABSTRACT

SAVanade is a miniature rose which can be grown quite satisfactorily in a greenhouse or as a hardy garden perennial. It blooms nearly continually throughout the growing season with buds and flowers of a bright yellow and having a mild fragrance. Blooms are most often borne singly on long, straight stems but also in small sprays. The plant, it self, grows 36 to 40 inches tall with an upright habit. This variety is completely thornless.

1 Drawing Sheet

BACKGROUND OF THE INVENTION

1. This invention is a rose plant of the miniature rose class which can be grown quite satisfactorily in a greenhouse, as a garden perennial, as a specimen plant, in a border, or for cut flowers, with protection recommended through the winter in severe climates.

2. This present invention is a new and distinct variety of miniature rose plant (*Rosa chinensis 'minima'*), which was created by crossing the following two rose plants: The seed parent is MORpoly, (U.S. Plant Pat. No. 8,453), a compact and prolific miniature rose, with medium yellow flowers, created by Ralph Moore. The pollen parent is MACgenev (U.S. Plant Pat. No. 8,279), a very fragrant, light pink, fully double hybrid tea rose created by Sam McGredy. The farietal denomination of this new rose is SAVanade.

3. The flowers of this present invention bear some resemblance in color and petalage to those of its seed parent, MORpoly, U.S. Plant Pat. No. 8,453. The stems of the new invention are completely without thorns, the flowers are more fragrant, and more flowers are borne singly and on longer stems when compared to those of MORpoly, U.S. Plant Pat. No. 8,453.

This new variety is distinguished by:

A. A completely thornless habit.

B. Flowers usually borne singly on stems averaging 6 to 10 inches long in summer and up to 24 inches long in the fall.

C. Buds and flowers of a bright yellow.

D. A plant that grows equally well in a greenhouse or out-doors; it is nearly always in bloom to serve as a decorative plant or for cut flowers.

E. Mild fragrance.

Asexual production by cuttings of this new variety as performed in Essex County, Mass. and in San Bernardino County, Calif. shows that all distinguishing characteristics of this rose continually come true to form.

SUMMARY OF THE INVENTION

This new variety has bright yellow flowers with a mild fragrance, borne mostly one-to-a-stem but also in small sprays of 3 to 5. The plant itself is completely thornless and grows in an upright, well branched habit to 36 to 40 inches tall at maturity. It can be grown quite satisfactorily in a greenhouse or as a hardy garden perennial requiring winter protection in severe climates.

BRIEF DESCRIPTION OF THE DRAWING

The accompanying color photograph shows specimens of the flowers of this new variety in different stages of development as seen and grown inside under plastic in late July in Essex County, Mass.

BOTANICAL DESCRIPTION OF THE PLANT

Following is a detailed description in outline form pertaining specifically to this new and distinct variety of miniature rose plant. All major color plate identifications made are referring to The Royal Horticulture Society Colour Chart except where common terms of color definition are employed.

Type: Miniature rose; hardy; outdoors; decorative; specimen plant; border plant; cut flower, potted plant; greenhouse.
Seed parent: MORpoly, U.S. Plant Pat. No. 8,453.
Pollen parent: MACgenev, U.S. Plant Pat. No. 8,279.
Flowers: Usually borne singly on stems averaging six to ten inches in length.
Quantity of bloom: abundant.
Bud:

*Size and form.*—Medium; ovate with acute tip.

*Sepals.*—Lanceolate, extending beyond the tip of the bud, very finely bearded with occasionally 1 or 2 flags on a side but in no pattern, rolling back individually to the stem as petals unfurl, and all back to the stem by the time the bloom is full open, remaining attached, then rolling back up as the hip matures; near 144A in color.

*Color when sepals first divide.*—Near 15B with near 15C.

*When petals begin to unfurl.*—Near 15B.

*Peduncle.*—Quite variable in length, averaging 1¼ inches; straight to very slightly curved; erect; near 144A in color sometimes flushed lightly with 182A.

Bloom:

*Size when fully expanded.*—About 2½ inches.

*Form.*—High centered at first, becoming flat; petals remaining loosely rolled outward and becoming ruffled at maturity.

*Petalage under normal conditions.*—17–25 with 0 to 5 petaloids in the center.

*Fragrance.*—Mild

Petals:

*Texture.*—Thick, inside velvety, outside satiny.

*Form.*—Spatulate.

*Arrangement.*—Regularly arranged shingle-like.

Color (From plants grown inside under plastic in Essex County, Mass., in late July 1997):

*During first two days.*—(Outer petals) inside surface — near 15C, reverse — between near 15B and 16A. (inner petals) inside surface — near 15A, reverse — between near 16A and near 15B.

*When half blown.*—(Outer petals) inside surface — between near 13B and near 15B with veins showing of near 15A, reverse — near 15D. (inner petals) inside surface near 14B, reverse — near 15C.

*Base of petals at attachment.*—15A.

*Color change as bloom ages.*—From near 15B with streaks of near 15C, to near 15C and near 15A towards center of the flower, then to near 14B with outer petals between 13B and 15B and veins showing of near 15A, then to near 14D and with veins of near 13B and with between 13C and 15C towards the center of the flower, then to near 11C with darker yellow veins and near 13B towards center of flower, and finally becoming near 11C with streaks near 11D and with near 9D towards the center of the flower.

*General tonality.*—Bright medium yellow; after three or more days — shades of medium and lighter yellows.

Lasting quality:

*On plant.*—3–5 days, before dropping cleanly.

*As a cut flower.*—5 to 9 days, depending on temperature.

Reproductive organs:

*Stamens.*—Average amount; arranged along upper, outer edge of receptacle.

*Filaments.*—Uneven lengths: 1/32 to ¼ of an inch; usually near 17B in color.

*Anthers.*—Near 16C in color.

*Pollen.*—Average amount; near 167A in color.

*Pistils.*—Average number.

*Styles.*—Uneven in length; near 182A in color.

*Stigmas.*—color near 4D.

*Hips.*—Usually pear shaped, up to 1⅛ inches long and up to 1 1/16 inches in diameter at the widest point; color near 25B when mature.

*Seeds.*—Up to 23 large seeds per hip with none protruding.

The plant:

*Habit.*—Upright, well branched.

*Growth.*—Vigorous, uniformly branched, 36 to 40 inches tall. Spread about 14 inches.

*Foliage.*—Medium, compound of mostly three to five (occasionally seven) leaflets. Color: new foliage, upper surface — near 146A and edges flushed with near 183C; underside — near 183A and 183B. Old foliage, upper surface — near 147A; underside— near 147B.

*Length of flowering stem.*—Averaging 6" to 10" when borne singly.

*Leaflet.*—Shape — acuminate; texture, upper surface — matte, under side — matte; edge — fine serration in a slightly irregular pattern.

*Rachis.*—Color, upper surface — near 147B, underside — near 144B;

*Stipules.*—About ⅛ of the length of the mature leaf; near smooth edges to very finely and sparsely bearded.

*New wood.*—Smooth with a color near 146B.

*Old wood.*—Near 147B and smooth.

*Resistance to diseases.*—Good.

*Thorns.*—This variety is completely thornless with no prickles or hairs.

The miniature rose plant and its flowers described herein may vary in detail due to climate, soil and cultural conditions under which the variety may be grown; the present description being of the new variety as grown inside under plastic in Essex County, Mass. in late July.

The following is claimed:

1. A new and distinct variety of miniature rose plant of hardy, upright, well branched habit, substantially as illustrated and described, characterized by bright yellow buds and flowers with a mild fragrance, borne mostly one-to-a-stem making them ideal for cut flowers; and further characterized by its complete lack of thorns, prickles or hairs, and easy to propagate from cuttings, with an abundant amount of dark green, matte foliage.

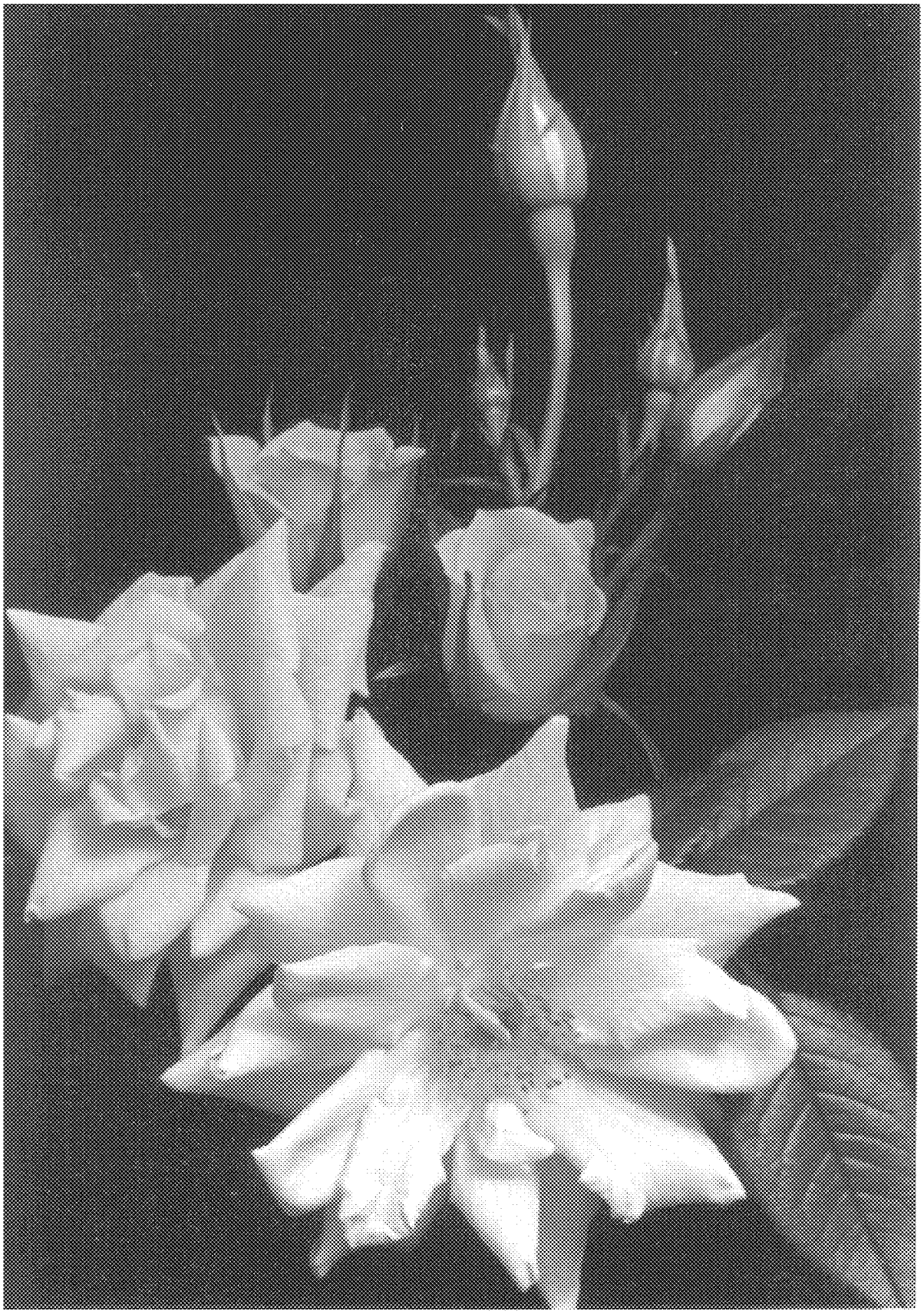

* * * * *